United States Patent [19]
Doi et al.

[11] Patent Number: 5,917,002
[45] Date of Patent: Jun. 29, 1999

[54] POLY(3-HYDROXYBUTANOIC ACID) FILM

[75] Inventors: Yoshiharu Doi; Tadahisa Iwata, both of Wako; Satoshi Kusaka, Hanyu, all of Japan

[73] Assignees: The Institute of Physical and Chemical Research; Akebono Research and Development Center Ltd., both of Saitama, Japan

[21] Appl. No.: 08/992,883

[22] Filed: Dec. 18, 1997

[30] Foreign Application Priority Data

Dec. 18, 1996 [JP] Japan .................................. 8-338382

[51] Int. Cl.$^6$ .......................... B29C 55/02; C08G 63/06
[52] U.S. Cl. .......................... 528/328; 435/132; 435/135; 435/136; 435/146
[58] Field of Search .............................. 528/328; 435/29, 435/132, 135, 136, 146

[56] References Cited

U.S. PATENT DOCUMENTS

| | | | |
|---|---|---|---|
| 4,738,811 | 4/1988 | Hara et al. | 264/211.12 |
| 5,585,249 | 12/1996 | Reusch | 435/29 |

FOREIGN PATENT DOCUMENTS

| | | |
|---|---|---|
| 0 078 609 A2 | 5/1983 | European Pat. Off. . |
| 0 104 731 A2 | 4/1984 | European Pat. Off. . |
| WO 94/16000 | 7/1994 | WIPO . |
| WO 97/22459 | 6/1997 | WIPO . |

*Primary Examiner*—Nathan M. Nutter
*Attorney, Agent, or Firm*—Knobbe, Martens, Olson & Bear, LLP

[57] ABSTRACT

Poly(3-hydroxybutanoic acid) having a number average molecular weight of not less than 500,000 is oriented at a draw ratio of 2-fold or more to reproducibly obtain a film made of poly(3-hydroxybutanoic acid) having biodegradability and biocompatibility as well as sufficient strength and flexibility (for example, tensile strength of not less than 30 MPa and elongation to break of not less than 15%).

6 Claims, 4 Drawing Sheets

Ori: REPLICATION ORIGIN,
Ap$^r$: AMPICILLIN RESISTANCE GENE,
stb: parB locus of PLASMID R1, A: AccI,
B: BamHI, C:ClaI, E:EcoRI, H:HindIII,
K: KpnI, N: NotI, P: PstI, Sa: SacI,
Sl: SalI, Sm: SmaI, Xb: XbaI, Xh: XhoI

POLY(3-HYDROXYBUTANOIC ACID) FILM

FIELD OF THE INVENTION

The present invention relates to a poly(3-hydroxybutanoic acid) film and a method of producing the same. More specifically, a biodegradable film having high tensile strength and break elongation and a method of producing the same.

BACKGROUND OF THE INVENTION

It is known that many microorganisms synthesize poly(3-hydroxybutanoic acid) (hereinafter sometimes referred to as "PHB") as an intracellular reserve substance which is accumulated in the form of granules in the cytoplasm (Anderson, A. J. And Dawes, E. A., Microbiol. Rev., 54: 450–472 (1990)). Recently, attention has been paid to PHB isolated from microbial cells as thermoplastic resin having biodegradability and biocompatibility (Doi, Y., In: Microbial polyesters. VCH. New York (1990)) and its application to formings such as films or fibers has been studied.

However, the conventional PHB homopolymer has not yet been put into practical use since it is physicochemically disadvantageous in its hardness and brittleness and is difficult to be used as formings by itself. On the other hand, it was found that the combination use of a 3-hydroxybutanoic acid with a copolymer component such as 3-hydroxypentanoic acid provides a flexible material having improved impact resistance and therefore, an attempt has been made to process copolymers that vary in their compositions into flexible films (see Holmes, P. A., Phys. Technol., 16, p32–36 (1985) and "Biodegradable Polymer Materials" Y. Doi ed., (Industrial Examination Committe, 1990) p. 27). However, methods of adding such a copolymer component may possibly be accompanied by the increased production cost, which would make economical performance worse. It was reported that an attempt was made to produce a film having high strength by subjecting PHB homopolymer to a orienting treatment, but not only it requires complicated conditions and a process having a number of steps but also it is not reproducible (Holmes, P. A., In: Developments in Crystalline Polymers-2, Bassett, D. C. (ed.), p1–65, Elsevier (1988)).

Accordingly, it has been desired to develop a method of simply and reproducibly producing a PHB film having improved physicochemical properties with retaining biodegradability.

SUMMARY OF THE INVENTION

An object of the present invention is to provide a method of producing a PHB film simply and reproducibly and such a film having improved physicochemical properties with retaining biodegradability.

As a result of intensive investigation, the present inventors have found that the above object can be achieved by using a specific PHB homopolymer having not less than a certain molecular weight, thereby completing the present invention.

Thus, the present invention relates to a method of producing a poly(3-hydroxybutanoic acid) film comprising the step of orienting poly(3-hydroxybutanoic acid) having a number average molecular weight of not less than 500,000 at a draw ratio of two-fold or more.

The present invention also relates to a film which is made of poly(3-hydroxybutanoic acid) having a number average molecular weight of not less than 500,000, and has tensile strength of not less than 30 MPa and elongation to break of not less than 15%.

The poly(3-hyroxybutanoic acid) film (hereinafter sometimes referred to as "PHB film") obtainable by the method of the present invention is much superior in physicochemical properties with retaining biodegradability to the conventional PHB and has improved physicochemical properties comparable to those of commonly used polymer (e.g., polypropylene, nylon-6, 6, etc.). Because of this, it is not necessary to formulate PHB into copolymer or polymer blend in order to improve its physicochemical properties and PHB homopolymer can be formed alone. Thus, it is also economically advantageous.

A PHB oriented film having biodegradability and biocompatibility as well as sufficient strength and flexibility can be obtained simply and reproducibly according to the present invention.

DETAILED DESCRIPTION OF THE INVENTION

The embodiments for carrying out the present invention will be described below.

(1) Method of Producing the Film of the Invention

The production method according to the present invention comprises the step of orienting poly(3-hydroxybutanoic acid) having a number average molecular weight (Mn) of not less than 500,000 at a draw ratio of two-fold or more.

(i) PHB having a number average molecular weight of not less than 500,000

According to the production method of the present invention, PHB having a number average molecular weight of not less than 500,000 is used as a material for forming into a film. In general, the methods of obtaining PHB include the fermentation synthetic method and the chemical synthetic method. The latter is the method of chemically synthesizing such PHB in accordance with the commonly used organic synthetic methods, thereby giving a mixture (racemate) of poly[(R)-3-hydroxybutanoic acid] and poly[(S)-3-hydroxybutanoic acid]. In contrast, the fermentation synthetic method comprises cultivating a microorganism capable of producing PHB and recovering PHB accumulated in the cells. PHB obtained by the fermentation synthetic method is poly[(R)-3-hydroxybutanoic acid] homopolymer.

In the present invention, it is preferable to use the fermentation synthetic method, by which only poly[(R)-3-hydroxybutanoic acid] homopolymer can be obtained, in view of the physicochemical properties of PHB obtained. Any microorganism can be used in the fermentation synthetic method as long as it is capable of producing PHB having a high molecular weight. It is known that PHB is accumulated in the cells of more than 60 species of naturally-occurring microorganisms including those belonging to the genus Alcaligenes such as *Alcaligenes eutrophus* or *Alcaligenes latus*. Particularly, the microorganism to be used in the present invention which produces high molecular weight PHB having a number average molecular weight of not less than 500,000 is strains of microbial species belonging to the genus Methylobacterium, more specifically, *Methylobacterium extorguens* ATCC55366 (Bourque, D. et al., Appl. Microbiol. Biotechnol. 44: 367–376 (1995)). These strains are commercially available from American Type Culture Collection (ATCC).

In the fermentation synthetic method, these microorganisms are generally cultivated in the usual culture medium containing a carbon source, a nitrogen source, inorganic ions, and, if necessary, other organic components to accumulate PHB in the microbial cells. PHB can be recovered from the microbial cells by extraction with an organic solvent such as chloroform, degradation of the microbial components with an enzyme such as lysozyme followed by collecting PHB granules by filtration, or the like method.

One of embodiments of the fermentation synthetic method comprises culturing a microorganism transformed with a recombinant DNA containing a PHB synthesis gene and recovering PHB produced in the microbial cells. In this method, unlike the case of culturing *Alcaligenes eutrophus* and the like as they are, microorganisms transformed with a recombinant DNA have no PHB hydrolysing enzyme and PHB having a remarkably high molecular weight can be accumulated. Therefore, it is particularly preferable in the present invention.

The metabolic system and enzymes involved in synthesis of PHB has been studied in detail in *Alcaligenes eutrophus* (see Haywood et al., FEMS Microbiol. Lett., 52: 91–96, 259–264 (1988), Haywood et al., FEMS Microbiol. Lett., 57: 1–6 (1989)). Namely, PHB is synthesized from acetyl-CoA through the action of three enzymes. First, two acetyl-CoA molecules are reversibly condensed by 3-ketothiolase to synthesize acetoacetyl-CoA. Acetoacetyl-CoA thus produced is reduced to (R)-3-hydroxybutyryl-CoA by acetoacetyl-CoA reductase bound to NADPH. Then, (R)-3-hydroxybutyryl-CoA is polymerized by PHB synthase to give PHB. Cloning and sequencing of the genes of these three enzymes of *Alcaligenes eutrophus* was already performed and it was elucidated that these genes constitute a biosynthesis operon containing phbC-phbA-phbB gene encoding synthase-thiolase-reductase, respectively (Steinbuchel, A. and Schlegel H. G., Mol. Microbiol., 5: 535–542 (1991)).

In the above-described PHB fermentation synthetic method using transformants, a recombinant DNA containing the PHB synthesis gene (hereinafter sometimes referred to as "phbCAB") of *Alcaligenes eutrophus* is transformed into a host. As the host, microbial species belonging to the genus Escherichia, specifically strains of *Escherichia coli*, can be used. Specific examples thereof include *Escherichia coli* XL1-Blue, JM109, DH5α, B, W, and the like. The above-described recombinant DNA containing phbCAB can be obtained by, for example, inserting phbCAB into a plasmid vector, a phage vector, or the like. Such vectors include pSYL, pUC, pBluescript, pJRD, pGEM, and the like plasmid vectors. The recombinant DNA can be transformed into the host by the conventional methods.

For example, transformant *Escherichia coli* XL1-Blue (pSYL105) used in Examples as described below which is obtained by transforming plasmid pSYL105 containing phb-CAB into *Escherichia coli* XL1-Blue can be produced in the following manner (see Lee, S. Y., et al., Biotechnol. Bioeng., 44: 1337–1374 (1994), Meynell, E. and Datta, N., Genet. Res. Camb., 7: 134–140 (1966), Rasmussen, P. B., et al., Mol. Gen. Genet., 209: 122–128 (1987), Gerdes, K., Bio/Technology, 6: 1402–1405 (1988), Schubert, P., et al., J. Bacteriol., 173: 168–175 (1991), Schubert, P., et al., J. Bacteriol., 170: 5837–5847 (1988), etc.).

Namely, plasmid pSYL105 is constituted by an EcoRI-HindIII fragment (0.6 kb) of pKG1022 (Gerdes, K., Bio/Technology, 6: 1402–1405 (1988)) having parB (hok/sok) locus derived from plasmid Rl (Meynell, E. and Datta, N., Genet. Res. Camb., 7: 134–140 (1966)), and an EcoRI-HindIII fragment (8.2 kb) of pSK2665 (Schubert, P. et al., J. Bacteriol., 173: 168–175 (1991)) having PHB synthesis operon phbCAB derived from *Alcaligenes eutrophus* H16 (ATCC17699) and ampicillin resistance gene. pKG1022 contributes to keep the plasmid stable and to give a large copy number. pSK2665 contributes to synthesize the three enzymes for synthesis of PHB (3-ketothiolase, NADPH-depending acetoacetyl-CoA reductase, and PHB synthase) and to selectively proliferate, by adding an antibiotic in the culture medium, desired recombinant *Escherichia coli* strains transformed with a recombinant DNA having drug resistance.

pKG1022 can be constructed as follows. Namely, 580 bp parB+ gene (derived from plasmid R1; its base sequence is described in FIG. 3 of Rasmussen, P. B., et al., Mol. Gen. Genet., 209: 122–128 (1987)) having an EcoRI-BamHI fragment is inserted into the multiple cloning region of pGEM3 (Promega, 3-6-18, Higashi-Nihonbashi, Chuo-ku, Tokyo, Japan) and an EcoRI-PvuII fragment (104 kb) of pGEM4 (Promega) containing the multiple cloning region is inserted into the EcoRI-PvuII region of pKG1020. The resulting transformant is designated as pKG1021. pKG1022 can be prepared by inserting the PstI fragment (containing Kanamycin resistance gene) derived from transposon Tn5 of *Escherichia coli* into the unique SmaI site of pKG1021.

pSK2665 can be constructed as follows. Namely, a 12.5 kb EcoRI fragment (PPI; Schubert, P. et al., J. Bacteriol., 170: 5837–5847 (1988)) derived from DNA of *Alcaligenes eutrophus* H16 (ATCC17699) is digested with restriction enzyme SmaI to obtain a 5.2 kb EcoRI-SmaI fragment (SE52; Schubert, P. et al., J. Bacteriol., 173: 168–175 (1991)). This fragment is inserted into plasmid pBluescript SK− (Toyobo; 17-9, Nihonbashi Koamicho, Chuo-ku, Tokyo, Japan) to give pSK2665.

The thus-obtained EcoRI-HindIII fragment (0.6 kb) of pKG1022 is inserted into the EcoRI-HindIl site of pSK2665 to give plasmid pSYL105.

The resulting plasmid pSYL105 is transformed into *Escherichia coli* XL1-Blue by the conventional method such as electroporation or the like to obtain a desired transformant.

The transformants are cultivated in an appropriate culture medium to allow them to accumulate PHB in the cells. Usable as the culture medium are those usually used containing carbon sources, nitrogen sources, inorganic ions, and, if necessary, other organic components. When *Escherichia coli* is used, glucose or the like is used as a carbon source and those derived from natural substances, such as yeast extract, trypton, or the like is used as a nitrogen source. In addition, the medium may contain an inorganic nitrogen-containing compound such as an ammonium salt or the like. The cultivation can be carried out under the aerobic conditions for 12 to 20 hours, at a cultivation temperature of 30 to 37° C., and at pH 6.0 to 8.0. PHB can be recovered from the microbial cells by extraction with an organic solvent such as chloroform or degradation of the microbial components with an enzyme such as lysozyme followed by collecting PHB granules by filtration, or the like method. Specifically, PHB can be extracted from the dried microbial cells, which are collected from the culture solution, with an appropriate poor solvent followed by precipitating it with a precipitating agent.

It was reported that the above mentioned *Escherichia coli* strain transformed with the recombinant DNA containing PHB synthesis gene phbCAB accumulated a large quantity of PHB (Slater et al., J. Bacteriol., 170: 4431–4436 (1988), Schubert et al., J. Bacteriol., 170: 5837–5847 (1988)). Recently, successful overproduction and purification of PHB synthase of *Alcaliqenes eutrophus* was reported (Gerngross et al., Biochemistry, 33: 9311–9320 (1994)). In vitro PHB synthesis using the isolated and purified PHB synthase resulted in PHB having a high molecular weight (Mn>10× $10^6$) that largely exceeds the molecular weight of PHB usually obtained from *Alcaligenes eutrophus* (Gerngross, T. U. and Martin, D. P., Proc. Natl. Acad. Sci. USA, 92: 6279–6283 (1995)). On the other hand, it is known that, in the cells of *Alcaligenes eutrophus*, PHB is hydrolyzed to (R)-3-hydroxybutanoic acid by intracellular hydrolases (Hippe, H. and Schlegel, H. G., Arch. Mikrobiol., 56: 278–299 (1967)). The time-course change of the molecular weight of PHB during its synthesis and hydrolysis was studied and its biosynthesis kinetic model was also proposed (Kawaguchi, Y., et al., Macromolecules, 25: 2324–2329 (1992), Koizumi F. and Doi Y., J. Macromol. Sci., Pure Appl. Chem., A32: 759–774 (1995)).

There is a report on the time-course change of the molecular weight of PHB synthesized using an *Escherichia* coli strain transformed with a recombinant DNA containing PHB synthesis gene phbCAB of *Alcaligenes eutrophus* (Kusaka et al., Polymer Preprints, Japan, vol. 45, No. 4 (1996)). According to the method using transformants in which a recombinant DNA has been inserted, PHB having a much higher molecular weight than that obtained by conventional cultivation of *Alcaligenes eutrophus* can be obtained. High molecular weight PHB to be used in the present invention has a number average molecular weight of not less than 500,000, preferably not less than 1,000,000, more preferably not less than 2,000,000. If the molecular weight is too small, it becomes difficult to carry out orienting at a high draw ratio and the resulting film cannot has sufficient strength. Though the upper limit of the number average molecular weight of PHB is not particularly limited, it is preferably not more than 20,000,000, more preferably not more than 15,000,000, in view of availability and forming characteristics.

The materials used for forming the film of the present invention include, in addition to the above-described PHB, for example, various additives usually used for forming a film, such as a lubricant, a ultraviolet absorbing agent, a weathering agent, an antistatic agent, an antioxidant, a heat stabilizer, a core agent, a fluidity-improving agent, a colorant, or the like, if necessary.

(ii) Orienting step

According to the method of the present invention, PHB having a number average molecular weight of not less than 500,000 as obtained by the above-described method is melted and drawn to form an oriented film. The method of orienting is not particularly limited and any orienting technique usually used for plastic films can be applied. Preferably, a film having a thickness of approximately 20 to 100 μm is made by the solvent cast method and the film is set at the drawing machine and oriented by applying tensile force in a certain direction under heating. An oil bath or the like is used for heating up preferably to a temperature of 155 to 180° C. In this occasion, when a film is immersed in the oil bath or the like, it generally becomes soft immediately. Thus, a weight or the like may be used for orienting. The film may be dissolved in the oil bath or the like if it is immersed therein for a long time. Accordingly, it is preferable to take out the film from the oil bath or the like immediately after it is oriented during immersion for 1 to 3 seconds. The orienting direction may be one direction (uniaxial orientation) or two directions (biaxial orientation). It is suitable in the present invention to orient in one direction.

The draw ratio is not less than 2-fold, preferably 2- to 10-fold, particularly preferably 4- to 10-fold. Drawing is not easy in the conventional method and a film is broken easily only at the draw ratio of less than 2-fold. In contrast, the method of the present invention enables orienting at such a high draw ratio because of using PHB having a high molecular weight. Thus, a film having high strength and flexibility can be produced. If the draw ratio is too low, the crystal orientation of PHB becomes weak and the strength is lowered, which is unfavorable. If the draw ratio is too high, the film is broken.

After orienting, the film is taken out from the oil bath and allowed to cool to room temperature to obtain a desired oriented film.

(iii) Heating step

The method of present invention may comprise the step of heating the oriented film obtained from the above orienting step subsequent to the orienting step. The temperature for the heating step ranges from 60 to 170° C., preferably 100 to 160° C. It is preferable to carry out the heat treatment under the conditions that tensile stress is applied so as to prevent the film from shrinking or deforming. Specifically, the oriented film obtained in the above orienting step is fixed on a corrective equipment or the like to undergo the heat treatment. It is carried out in the air. The period of the heat treatment ranges preferably from 20 minutes to 2 hours. By conducting such a heat treatment, tensile strength and elongation to break can be further improved.

When the heat treatment is carried out, it is particularly preferable to use a film made of PHB having a number average molecular weight of not less than 2,000,000 since the resulting effect is outstanding. Physicochemical properties such as tensile strength or elongation to break are further improved in the case of the film made of PHB having a number average molecular weight of not less than 2,000,000. On the contrary, in the case of the film made of PHB having a number average molecular weight of less than 2,000,000, its physicochemical properties may possibly become worse because its molecular weight is reduced by pyrolysis during the heat treatment.

(2) Film of the Present Invention

The film of the present invention is a film which is made of PHB (poly(3-hydroxybutanoic acid)) having a number molecular weight of not less than 500,000, and has tensile strength of 30 MPa or more and elongation to break of 15% or more.

Conventionally, PHB homopolymer is physicochemically disadvantageous in its hardness and brittleness. It is hardly formed into a film. The present invention can provide a film made of PHB homopolymer, having physicochemical properties comparable or superior to the conventionally used polymers.

The term "tensile strength" used herein means the value measured in accordance with JIS(Japanese Industrial Standard)-K-6301. The film of the present invention shows tensile strength of 30 MPa or more, preferably 50 MPa or more. The elongation to break is measured in accordance with JIS-K-6301 and is 15% or more, preferably 30% or more. The melting point of the PHB film of the present invention is preferably 175° C. or higher, more preferably 182 to 186° C.

Further, the film of the present invention has flexibility comparable or superior to the polymers commonly used for forming a film. For example, Young's modulus is not more than 3 GPa, more preferably 0.5 to 2 GPa.

The film having such physicochemical properties can be obtained by orienting high molecular weight PHB having a number average molecular weight of not less than 500,000 by the above-described method. PHB having a number average molecular weight of not less than 500,000 can be obtained by the above-described fermentation synthetic method or the like.

The film of the present invention is an oriented crystalline film in which the orientation of crystals of the PHB film is in the constant direction. Since it is difficult for the conventional PHB to provide oriented crystals, it is not easy to obtain an oriented crystalline film. The present invention can provide an oriented crystalline film by orienting PHB having a high molecular weight of more than a certain level. The film of the present invention preferably has crystallinity of 75% or more.

As described above, the film of the present invention has sufficient strength and flexibility and is made of PHB which is excellent in biodegradability and biocompatibility. Therefore, the present film is useful for medical equipments, wrapping materials for food or others, a plastic sheet for agricultural use, pots for seedlings, sheets for use in construction, and the like.

EXAMPLES

Examples of the present invention will be illustrated below.

Production Example

[Synthesis of PHB]

(1) Preparation of transformants (*Escherichia coli* XL1-Blue (pSYL105))

pKG1022 (0.6 kb) containing parB (hok/sok) locus derived from plasmid R1 was prepared in the following manner (Gerdes, K., Bio/Technology, 6: 1402–1405 (1988)). Namely, 580 bp parB$^+$ gene having an EcoRI-BamHI fragment (for the gene sequence see Rasmussen, P. B. et al., Mol. Gen. Genet., 209: 122–128 (1987)) was inserted into the multiple cloning region of pGEM3 (Promega) and the EcoRI-PvuII fragment (104 kb) of pGEM4 (Promega) containing the multiple cloning region was inserted into the EcoRI-PvuII region of pKG1020. This was named pKG1021. pKG1022 was prepared by inserting the PstI fragment (containing the Kanamycin resistance gene) derived from *Escherichia coli* transposon Tn5 into the unique SmaI site of pKG1021.

Separately, pSK2665 containing PHB biosynthesis operon of *Alcaliaenes eutrophus* H16 (ATCC17699) was prepared in the following manner (Schubert, P. et al., J. Bacteriol., 173: 168–175 (1991)). Namely, a 12.5 kb EcoRI fragment (PPI: Schubert, P. et al., J. Bacteriol., 170: 5837–5847 (1988)) derived from DNA of *Alcaligenes eutrophus* H16 (ATCC17699) was digested with restriction enzyme SmaI to obtain a 5.2 kb EcoRI-SmaI fragment (SE52: Schubert, P. et al., J. Bacteriol., 173: 168–175 (1991)). This fragment was inserted into plasmid pBluescript SK$^-$ (Toyobo) to give pSK2665.

Figure 1:
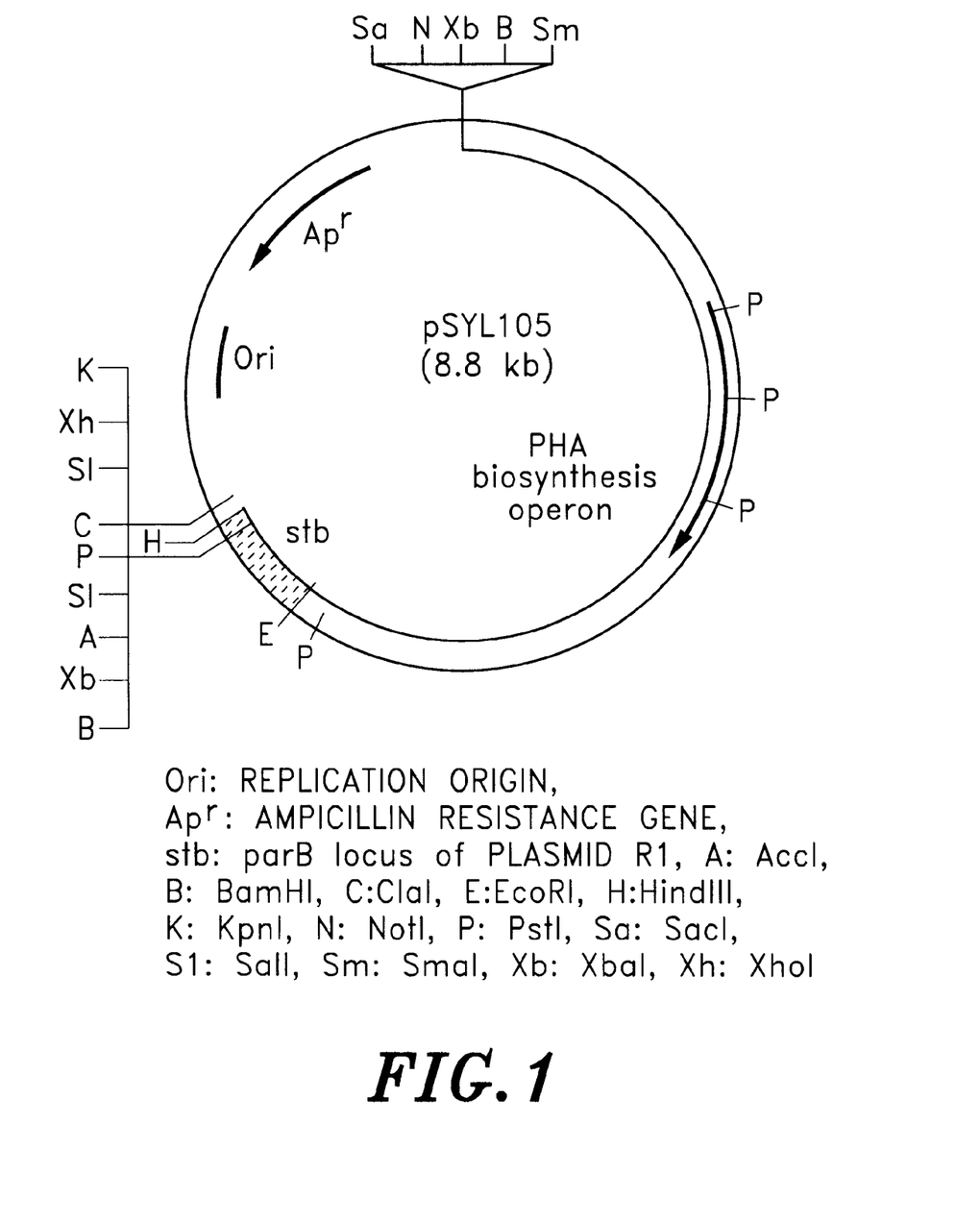
FIG. 1 shows the structure of plasmid pSYL105 obtained in Production Example.

Plasmid pSYL105 (8.8 kb) was obtained by inserting the EcoRI-HindIII fragment (0.6 kb) of pKG1022 into the EcoRI-HindIII site of pSK2665. The structure of the thus-obtained plasmid pSYL105 is shown in FIG. 1 (See Lee, S. Y. et al., Biotechnol. Bioeng., 44: 1337–1347 (1994)).

Transformation of plasmid pSYL105 into *Escherichia coli* XL1-Blue was effected by electroporation to give transformants (*Escherichia coli* XL1-Blue (pSYL105)). *Escherichia coli* XL1-Blue was obtained from Stratagene Cloning System (11011 North Torrey Pines Road, La Jolla, Calif. 92037, USA).

(2) Fermentation synthesis (i) Preculture

A 20-mL test tube containing 3.5 mL of Luria-Bertani (LB) medium containing yeast extract 5 g/L, trypton 10 g/L, and sodium chloride 10 g/L was inoculated with 1 mL of 10%(v/v) glycerol stock of *Escherichia coli* XL1-Blue (pSYL105) which was stored at −80° C. and cultivated at 37° C. for 12 hours under aerobic conditions. This was inoculated to 75 mL of LB medium in a 500-mL Sakaguchi flask and cultivated at 37° C. for 12 hours under aerobic conditions. The important thing in this preculture is not to add glucose.

(ii) Main culture 1335 mL of LB medium was added to Marubishi Bioengi Model 250 followed by sterilization at 121° C. for 15 minutes. Separately, a solution of glucose 30 g/water 100 mL was sterilized under the same conditions as above and added to a fermentor. The fermentor was adjusted to a temperature of 37° C. with supplying filter-sterilized air at 0.75 L/min and agitating at 400 rpm. The pH of the medium was automatically controlled at 6.0 to 7.0 with 2N NaCl and 2N $H_2SO_4$ under monitoring of the pH. 75 mL of culture obtained from the preculture was inoculated thereto. Cultivation was carried out for 12 to 15 hours and the culture was recovered.

(3) Recovering of microbial cells

The culture solution thus recovered was subjected to centrifugation at 4° C. and at 15,000 g for 10 minutes to remove the supernatant. The recovered microbial cells was washed by mixing well with distilled water and the resulting washings were centrifuged again for separation. The collected microbial cells was subsequently lyophilized.

The thus-obtained dried cells were ground well and added to chloroform maintained at room temperature to give a ratio of about 5 g of cells per 2 L of chloroform and mixed well. After PHB was completely extracted into chloroform, the cells were removed by filtration. The filtrate was concentrated about one tenth using a rotary evaporator. The concentrate was slowly poured into 10-fold volume of hexane to obtain white precipitate of PHB. Hexane was removed by filtration and the precipitate was dried well to give the desired PHB.

The number average molecular weight (Mn) of the obtained PHB was measured at 40° C. using Shimadzu 10A GPC system, 6A differential refractometer, with joint columns of Shodex K802 and K806M. Elution was carried out using chloroform as an eluent at the flow rate of 0.8 mL/min. The sample concentration was 0.25 mg/mL. The calibration curve was prepared using polystyrene standard having a number average molecular weight of 1,200 to 2,900,000 which showed narrow polydispersity and the molecular weight was calculated from the data obtained through GPC by applying GPC program with Shimadzu chromatopack C-R7A. Possible error in the molecular weight measurement was ±20%. In this way, PHBs having the number average molecular weight of 300,000, 750,000, 1,000,000, 2,000,000, 6,000,000, and 14,000,000 were obtained (see Tables 1 to 2 below).

COMPARATIVE EXAMPLES 1 to 2, EXAMPLES 1 to 9

Figure 2:
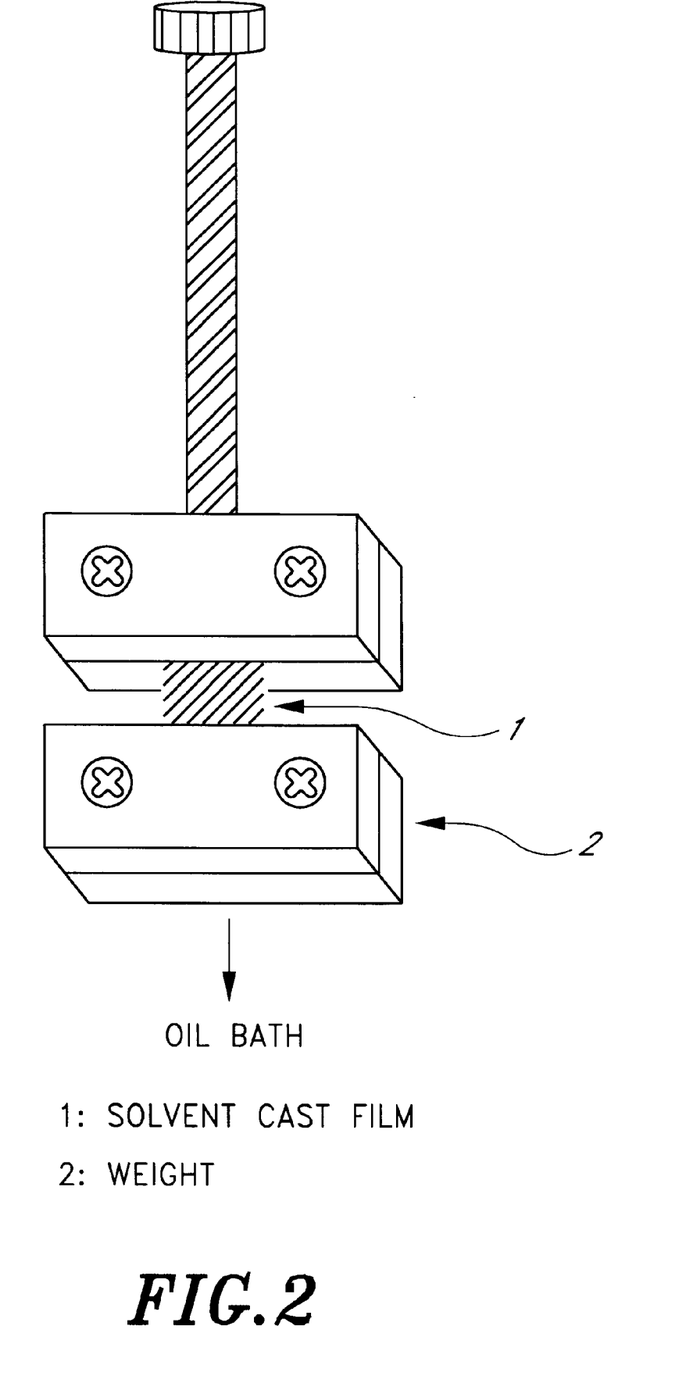
FIG. 2 schematically shows a state in which the film is set on the drawing machine used in Examples 1 to 9.

Using PHB as obtained in Production Example above having the number average molecular weight shown in Table 1, a film having a thickness of 50 μm was made by the solvent cast method (solvent: chloroform, concentration: 1%(wt/v)) and the film was cut into a size of 10×20 mm to serve as a test film (Comparative Examples 1 to 2 and Examples 1 to 9). The test film was set on the drawing machine with the weight corresponding to the draw ratio and immersed in an oil bath for 1 to 3 seconds. FIG. 2 schematically shows a state in which the test film is set on the drawing machine. In FIG. 2, 1 stands for the test film and 2 stands for the weight. The draw temperature (oil bath temperature) was adjusted depending on the PHB used as shown in Table 1.

The test film was softened immediately after it was immersed in the oil bath and oriented by the weight. Table 1 shows the draw ratio for each film. The thus-obtained oriented film was quickly taken out from the oil bath and allowed to cool at room temperature. In the case of using PHB having the number average molecular weight of 300,000 (Comparative Examples 1 to 2), the film was cut in the oil bath and could not be oriented.

The resulting oriented films were measured for tensile strength, elongation to break, and Young's modulus. The results are shown in Table 1. Tensile strength, elongation to break, and Young's modulus were measured in accordance with JIS-K6301 using SV-200 Model tensile compression test machine manufactured by Imada Seisakusho. The shape of the sample used was a dumbbell type having size 4 according to JIS-K6301 and the tensile rate was 20 mm/min.

As can be seen from the results, the method of the present invention can provide PHB film having such excellent physicochemical properties as high tensile strength and elongation to break.

derived extracellular PHB hydrolase was used. The enzyme was added to 50 mM Tris-HCl buffer having pH 7.5 so as to give a concentration of 10 μg/ml. Each film having a size and thickness of 5 mm×10 mm×0.02 mm was added thereto to react at 37° C. After 20 to 30 hours, every film was completely hydrolyzed.

EXAMPLE 20

Using PHB as obtained in Production Example above, the following films (PHB(1), PHB(2), and PHB (3)) were pre-

TABLE 1

|  | Mn | Draw temperature (° C.) | Draw ratio (%) | Tensile strength (MPa) | Elongation to break (%) | Young's Modulus (GPa) |
|---|---|---|---|---|---|---|
| Comparative Example 1 | 300,000 | 158 | cannot be oriented | — | — | — |
| Comparative Example 2 | 300,000 | 162 | cannot be oriented | — | — | — |
| Example 1 | 750,000 | 159 | 250 | 35 | 15 | 1.5 |
| Example 2 | 1,000,000 | 162 | 700 | 30 | 32 | 0.6 |
| Example 3 | 1,000,000 | 163 | 980 | 82 | 33 | 1.5 |
| Example 4 | 2,000,000 | 161 | 510 | 51 | 42 | 1.1 |
| Example 5 | 2,000,000 | 164 | 880 | 57 | 43 | 1.4 |
| Example 6 | 6,000,000 | 165 | 630 | 62 | 58 | 1.0 |
| Example 7 | 6,000,000 | 161 | 740 | 67 | 58 | 1.2 |
| Example 8 | 14,000,000 | 162 | 600 | 71 | 66 | 1.1 |
| Example 9 | 14,000,000 | 164 | 950 | 70 | 64 | 0.9 |

EXAMPLES 10 to 18

Using PHB as obtained in Production Example above having the number average molecular weight shown in Table 2, oriented films were prepared in the same manner as in Examples 1 to 9. The draw ratio was as indicated in Table 2. The oriented films thus obtained were fixed on the corrective equipment to prevent the films from shrinking and deforming and heat-treated at 160° C. for 2 hours in the air. The number average molecular weight of PHB in the oriented film after the heat treatment is shown in Table 2. The tensile strength, elongation to break, and Young's modulus were also measured in the same manner as in Example 1. The results are shown in Table 2.

From the results, it can be found that physicochemical properties of the oriented films of PHB having the number average molecular weight of not less than 2,000,000 can be improved by the heat treatment under certain conditions compared with those before the heat treatment.

pared in the same manner as in Examples 1 to 9. The heat treatment was carried out in the same manner as in Examples 10 to 18. Non-oriented films were prepared in the same manner as the test films before the orienting treatment in Examples 1 to 9.

PHB(1): number average molecular weight, 300,000; non-oriented.

PHB(2): number average molecular weight, 6,000,000; draw ratio, 620%.

PHB(3): number average molecular weight, 6,000,000; draw ratio, 620%; heat treatment, at 160° C. for 2 hours.

The resulting PHB films and those conventionally used as a film material, including high density polyethylene, polypropylene, polyethylene telephthalate (PET), and polyamide resin (nylon-6,6), were examined for melting point (Tm: °C.), glass transition point (Tg: °C.), crystallinity (%), Young's modulus (GPa), tensile strength (MPa), and elongation to break (%). The results are shown in Table 3.

TABLE 2

|  | Mn | Mn after heat-treatment | Draw ratio (%) | Tensile strength (MPa) | Elongation to break (%) | Young's Modulus (GPa) |
|---|---|---|---|---|---|---|
| Example 10 | 750,000 | 570,000 | 250 | — | — | — |
| Example 11 | 1,000,000 | 710,000 | 640 | 42 | 18 | 1.4 |
| Example 12 | 1,000,000 | 710,000 | 820 | 37 | 18 | 1.3 |
| Example 13 | 2,000,000 | 1,500,000 | 630 | 50 | 65 | 1.4 |
| Example 14 | 2,000,000 | 1,500,000 | 900 | 48 | 63 | 1.5 |
| Example 15 | 6,000,000 | 4,500,000 | 560 | 89 | 67 | 2.2 |
| Example 16 | 6,000,000 | 4,500,000 | 900 | 62 | 67 | 1.5 |
| Example 17 | 14,000,000 | 8,000,000 | 660 | 67 | 71 | 1.9 |
| Example 18 | 14,000,000 | 8,000,000 | 950 | 74 | 74 | 2.4 |

EXAMPLE 19

The oriented PHB film (Example 7) and the same film after heat treatment (Example 16) were applied to enzymatic hydrolysis assay. As the hydrolase, *Alcaligenes faecalis*-

From the results, the oriented PHB film according to the present invention had sufficient strength and flexibility comparable to those of polymers for conventionally used plastics.

TABLE 3

|  | High density polyethylene | Polypropylene | Polyethylene telephthalate | Nylon-6,6 | PHB(1)*[1] | PHB(2)*[2] | PHB(3)*[3] |
|---|---|---|---|---|---|---|---|
| Melting point (° C.) | — | 176 | 267 | 265 | 178 | 182 | 186 |
| Glass transition point (° C.) | — | −10 | 69 | 50 | 4 | 5 | 2.2 |
| Crystallinity (%) | — | 50–70 | 30–50 | 40–60 | 60–80 | 80 | >90 |
| Young's modulus (GPa) | — | 1.7 | 2.9 | 2.8 | 3.5 | 1 | 1.7 |
| Tensile strength (MPa) | 22–28 | 38 | 70 | 83 | 40 | 60 | 80 |
| Elongation to break (%) | 15–100 | 40 | 100 | 60 | 6 | 55 | 70 |

*[1] PHB(1): non-oriented, number average molecular weight, 300,000.
*[2] PHB(2): draw ratio, 620%; number average molecular weight, 6,000,000.
*[3] PHB(3): draw ratio, 620%; heat treatment, at 160° C. for 2 hours; number average molecular weight, 6,000,000.

EXAMPLE 21

X-ray diffraction was carried out for analysis molecular orientation in the oriented film obtained in Example 16. For X-ray diffraction, exposure was carried out for 6 hours by using Laue camera (transmission method), CuK$^\alpha$ monochromized by Ni filter as the X-ray source under the conditions of camera length of 3.85 cm, 40 KV, and 30 mA.

Figure 3:
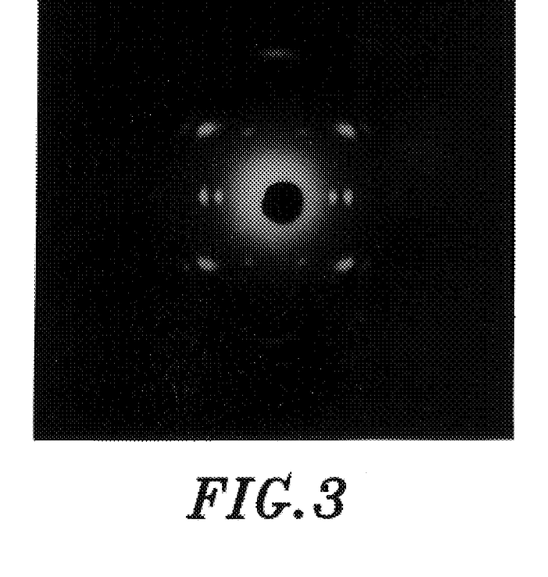
FIG. 3 is an X-ray photograph of the oriented film of Example 21.
Figure 4:
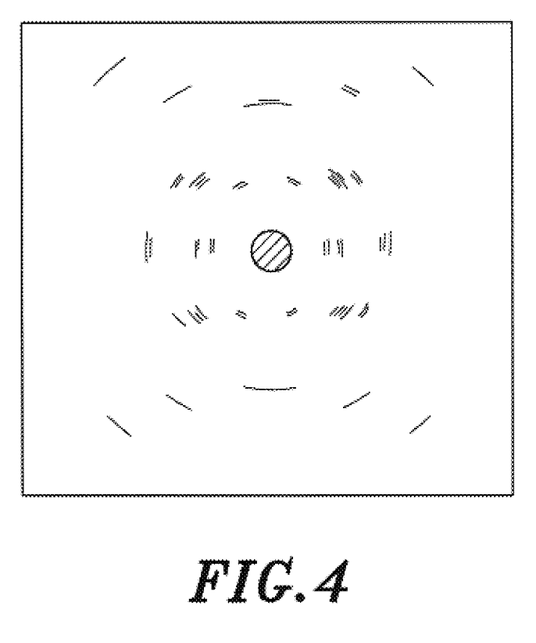
FIG. 4 schematically shows an X-ray photograph of diffraction pattern of the oriented film of Example 21.
Figure 5:
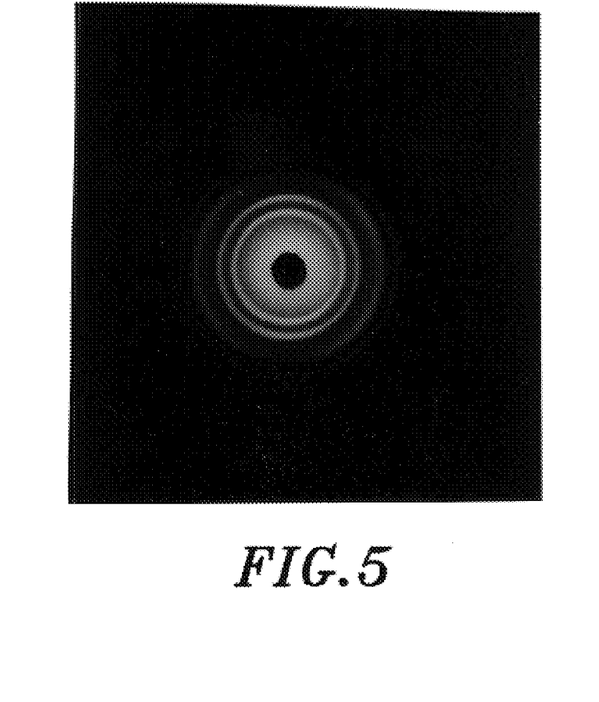
FIG. 5 shows an X-ray photograph of the non-oriented film of Example 21.
Figure 6:
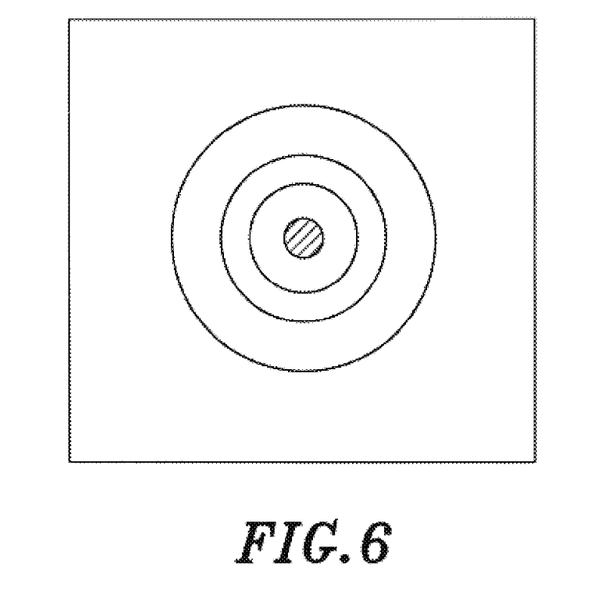
FIG. 6 schematically shows an X-ray photograph of diffraction pattern of the non-oriented film of Example 21.

The results are shown in FIGS. 3 and 4. FIG. 3 is the X-ray photograph and FIG. 4 schematically shows its diffraction pattern. From these figures, it can be found that the oriented film of the present invention has oriented crystallinity. The non-oriented PHB film was also subjected to X-ray photographing in the same manner. FIG. 5 shows the X-ray photograph of this non-oriented film and FIG. 6 schematically shows its diffraction pattern. No diffraction point but ring pattern is observed in the non-oriented film.

What is claimed is:

1. A method of producing a poly(3-hydroxybutanoic acid) film, which is biodegradable and which has a tensile strength of not less than 30 MPa and a breaking extension of not less than 15%, comprising the steps of obtaining a non-stretched film made of poly(3-hydroxybutanoic acid) homopolymer having a number average molecular weight of not less than 500,000; and stretching the non-stretched film at a draw ratio of two-fold or more.

2. The method as claimed in claim 1, wherein said orienting is carried out at a temperature ranging from 155 to 180° C.

3. The method as claimed in claim 1, wherein said poly(3-hydroxybutanoic acid) having a number average molecular weight of not less than 500,000 is obtained by cultivating a microorganism transformed with a recombinant DNA containing a poly(3-hydroxybutanoic acid) synthesis gene and recovering poly(3-hydroxybutanoic acid) produced in the microbial cells.

4. The method as claimed in claims 1, further comprising the step of heating the oriented film obtained from the orienting step at a temperature of 60 to 170° C.

5. A biodegradable stretched film made of poly(3-hydroxybutanoic acid) homopolymer haing a number average molecular weight of not less than 500,000, which has a tensile strength of not less than 30 MPa and a breaking extension of not less than 15%.

6. The film as claimed in claim 5, which is a crystalline film in which said poly(3-hydroxybutanoic acid) is oriented in one direction.

* * * * *